US010788237B2

(12) United States Patent
Sayeki

(10) Patent No.: US 10,788,237 B2
(45) Date of Patent: Sep. 29, 2020

(54) WIND DIRECTION ADJUSTING APPARATUS OF AIR-CONDITIONING BLOWOUT PORT, AND ANTIBACTERIAL MEMBER

(71) Applicant: Goro Sayeki, Tokyo (JP)

(72) Inventor: Goro Sayeki, Tokyo (JP)

(*) Notice: Subject to any disclaimer, the term of this patent is extended or adjusted under 35 U.S.C. 154(b) by 246 days.

(21) Appl. No.: 15/560,341

(22) PCT Filed: Mar. 27, 2015

(86) PCT No.: PCT/JP2015/059788
§ 371 (c)(1),
(2) Date: Sep. 21, 2017

(87) PCT Pub. No.: WO2016/157338
PCT Pub. Date: Oct. 6, 2016

(65) Prior Publication Data

US 2018/0073766 A1 Mar. 15, 2018

(51) Int. Cl.
*F24F 13/08* (2006.01)
*A61L 9/015* (2006.01)
(Continued)

(52) U.S. Cl.
CPC ............ *F24F 13/085* (2013.01); *A61L 9/015* (2013.01); *F24F 1/0047* (2019.02); *F24F 13/14* (2013.01);
(Continued)

(58) Field of Classification Search
CPC .......... F24F 13/085; F24F 13/14; F24F 13/20; F24F 1/0047; F24F 2003/1675; A61L 9/015; A61L 2209/134
(Continued)

(56) References Cited

U.S. PATENT DOCUMENTS 3,210,901 A * 10/1965 Meyer ..................... E04D 3/357 52/511
4,813,344 A 3/1989 Greif
(Continued)

FOREIGN PATENT DOCUMENTS

CN 204072861 U 1/2015
JP 11-132488 5/1999
(Continued)

OTHER PUBLICATIONS

Search Report in international Application No. PCT/JP2015/059788 dated Jun. 23, 2015, 6 pages
(Continued)

*Primary Examiner* — Steven B McAllister
*Assistant Examiner* — Allen R Schult
(74) *Attorney, Agent, or Firm* — Marshall, Gerstein & Borun LLP

(57) ABSTRACT

A wind direction adjusting apparatus of an air-conditioning blowout port is equipped with: a face plate portion which is disposed in the front of the air-conditioning blowout port from which the air conditioned by an air conditioner is blown out, and receives the air blown from the air-conditioning blowout port; a mounting portion which mounts the face plate portion forward of the air-conditioning blowout port; and an antibacterial member which is mounted to the face plate portion. The antibacterial member has: an antibacterial agent which is a material having bactericidal properties; a bag body which contains the antibacterial agent in a bag material with pores on the entire surface; and a housing which contains the bag body and has a vent hole that limits the ventilation volume of air blown out from the air-conditioning blowout port and passing through the bag body.

6 Claims, 3 Drawing Sheets

5 7 11 12 6 7 14 13 10R 9 12 10C 1 7 9 12 10L 8 4

(51) Int. Cl.

| | |
|---|---|
| ***F24F 13/20*** | (2006.01) |
| ***F24F 13/14*** | (2006.01) |
| ***F24F 1/0047*** | (2019.01) |
| ***F24F 3/16*** | (2006.01) |

(52) U.S. Cl.
CPC ......... *F24F 13/20* (2013.01); *A61L 2209/134* (2013.01); *F24F 2003/1675* (2013.01)

(58) Field of Classification Search
USPC .......................................................... 454/358
See application file for complete search history.

(56) References Cited

U.S. PATENT DOCUMENTS

| | | | |
|---|---|---|---|
| 5,775,876 A | 7/1998 | Walker et al. | |
| 6,241,219 B1 | 6/2001 | Logan et al. | |
| 6,386,971 B1 * | 5/2002 | Johnson | A61L 9/12 422/124 |
| 2011/0126917 A1 * | 6/2011 | Nakata | F24F 1/0007 137/268 |

FOREIGN PATENT DOCUMENTS

| | | |
|---|---|---|
| JP | 2000-247806 | 9/2000 |
| JP | 2002-213805 | 7/2002 |
| JP | 2003-021389 | 1/2003 |
| JP | 3114170 | 9/2005 |
| JP | 2012-090743 | 5/2012 |
| JP | 2014-111474 | 6/2014 |
| JP | 2015-012865 | 1/2015 |

OTHER PUBLICATIONS

Office Action in CN Application No. 201580078301.9 dated May 7, 2019, 20 pages.

* cited by examiner

WIND DIRECTION ADJUSTING APPARATUS OF AIR-CONDITIONING BLOWOUT PORT, AND ANTIBACTERIAL MEMBER

TECHNICAL FIELD

The present application discloses a wind direction adjusting apparatus at an air conditioning blowout port, and an antibacterial member.

BACKGROUND ART

In recent years, a variety of architectural structures instanced by buildings, shops, hospitals, and houses are installed with air conditioners that air-condition the insides of the rooms. The air conditioners are, though classified into a type of being embedded in ceilings, walls and other equivalent portions, a type of being suspended from the ceilings and a type of being installed on wall surfaces, common in terms of each being equipped with an air conditioning blowout port from which air being air-conditioned is blown into an inside of a room.

Incidentally, a specific gravity of air is inversely proportional to a temperature, and hence warm air collectively stays in an upper portion of an inside of a room. While on the other hand, cool air collectively stays in a low portion in the inside of the room. Accordingly, the air conditioner, when performing, e.g., a cooling operation, blows the cool air toward the lower portion in the inside of the room from an air conditioning blowout port so as to enable the warm air to be air-conditioned by efficiently sucking the warm air collectively staying in the upper portion of the inside of the room. Accordingly, for preventing the cold air blown out of the air conditioning blowout port from blowing against a person in the inside of the room, such instruments are commercially available as to adjust a wind direction of the air conditioning blowout port as illustrated in, e.g., Patent document 1.

DOCUMENTS OF PRIOR ARTS

Patent Document

[Patent document 1] Japanese Utility Model Registration Publication No. 3114170

SUMMARY OF THE INVENTION

Problems to be Solved by the Invention

In recent years, news media have been reporting herd infections of infectious diseases and mass food poisoning had occurred, and public hygiene awareness is on the verge of rising. Then, there are developed a variety of spatial sterilizing goods for sterilizing disease-causing bacteria floating in an inside of a room.

By the way, a majority of spatial sterilizing goods developed hitherto are roughly classified into mechanical apparatuses having built-in blowers and other equivalent devices for actively diffusing a sterilizing substance, and simply-structured products for passively diffusing the sterilizing substance. The former mechanical apparatuses are, however, generally more expensive than the latter simply-structured products, and are ambiguous about whether the sterilizing substance spreads over in the inside of the room as performance indicates because of being affected by an air flow from an air conditioning blowout port provided in the inside of the room. The latter simply-structured products are, though less expensive than the former mechanical apparatuses, hard to say that sufficient sterilizing performance is exhibited because the diffusion of the sterilizing substance depends on an ambient airflow.

Under such circumstances, the present application aims at providing a technology enabled to effectively diffuse a sterilizing substance to an inside of a room with a simple configuration.

Means for Solving the Problems

To solve the problems described above, according to the present invention, an antibacterial member with an antibacterial agent being contained in an enclosure having vent holes regulating a ventilation quantity of air, is disposed in a faceplate for a wind direction adjusting apparatus including the faceplate being disposed in front of an air conditioning blowout port from which air being air-conditioned by an air conditioner is blown, and receiving the air blown out of the air conditioning blowout port.

Specifically, a wind direction adjusting apparatus at an air conditioning blowout port, includes: a faceplate being disposed in front of the air conditioning blowout port from which air being air-conditioned by an air conditioner is blown, and receiving the air blown out of the air conditioning blowout port; a fitting portion fitting the faceplate to a front portion of the air conditioning blowout port; and an antibacterial member being fitted to the faceplate and including: an antibacterial agent as a substance having a bactericidal property; a bag body having a bag material formed with minute holes over an entire surface, and containing the antibacterial agent; and an antibacterial member accommodating the bag body and having vent holes regulating a ventilation quantity of air permeating the bag body by being blown out of the air conditioning blowout port.

The wind direction adjusting apparatus described above enables diffusion of the sterilizing substance by a flow of the air forcibly blown out of the air conditioning blowout port of the air conditioner, and has therefore no necessity for preparing a mechanical apparatus having built-in blowers and other equivalent machines for diffusing the sterilizing substance. It is feasible to diffuse the antibacterial substance in a room space throughout more surely than a simply structured product that passively diffuses the sterilizing substance, and sufficient disinfection performance can be therefore expected. The enclosure accommodating the bag body regulates a ventilation quantity of the air permeating the bag body, and the antibacterial agent is thereby enabled to stably continue exhibiting its efficacy by restraining a control-release quantity from fluctuating even when an airflow rate from the air conditioning blowout port varies corresponding to an operation state of the air conditioner.

The antibacterial agent may be a particulate antibacterial agent with chlorine dioxide borne on a porous inorganic solid carrier, and the bag material may have minute holes, on the entire surface, each having a diameter smaller than a particle size of the inorganic solid carrier. When using an agent with chlorine dioxide adsorbed to a porous carrier, chlorine dioxide dissociates from surfaces of fine particles due to the airflow of the air flowing into the enclosure from the air conditioning blowout port, and is released outside of the bag body via the minute holes formed in the entire surface of the bag body. Chlorine dioxide is released into the gap within the enclosure, and is control-released outside of the enclosure 16 from the vent holes that regulate the ventilation quantity.

The antibacterial member may be placed on an upper surface of the faceplate, and the vent holes may be formed in an enclosure in an elliptical shape with a longitudinal direction extending along a flow direction of the air blown out of the air conditioning blowout port. The antibacterial member may also be placed on the upper surface of the faceplate, and the vent holes may also be formed in a side surface, of a plurality of side surfaces of the enclosure, on an upstream side opposite to the flow of the air blown out of the air conditioning blowout port and a side surface on a downstream side positioned on an opposite side to the side surface on the upstream side. The wind direction adjusting apparatus including the antibacterial member described above causes the air blown out of the air conditioning blowout port to swiftly circulate inside and outside of the enclosure, and hence the sterilizing substance is properly control-released.

The antibacterial member may be a member having a thin plate-like external shape. The wind direction adjusting apparatus including the antibacterial member described above, since the flow of the air blown out of the air conditioning blowout port is hard to be disturbed, enables a proper adjustment of a direction of the air blown out of the air conditioning blowout port.

The enclosure may be provided with a hook and loop fastener detachably attachable to the faceplate. The wind direction adjusting apparatus such as this facilitates replacing the antibacterial member.

The fitting portion may have an angle adjusting portion enabled to adjust a fitting angle of the faceplate with respect to the air conditioning blowout port. The wind direction adjusting apparatus such as this is capable of adjusting the air blown out of the air conditioning blowout port in a desired direction.

It is to be noted that the present invention maybe grasped in terms of an aspect as an antibacterial member. To be specific, according to the present invention, an antibacterial member being fitted to a faceplate of a wind direction adjusting apparatus including the faceplate being disposed in front of an air conditioning blowout port from which air being air-conditioned by an air conditioner is blown, and receiving the air blown out of the air conditioning blowout port, includes: an antibacterial agent as a substance having a bactericidal property; a bag body having a bag material formed with minute holes over an entire surface, and containing the antibacterial agent; and an enclosure accommodating the bag body and having vent holes regulating a ventilation quantity of air being blown out of the air conditioning blowout port and permeating the bag body.

Effects of the Invention

According to the present invention, it is feasible to effectively diffuse the sterilizing substance in the inside of the room with a simple configuration.

MODE FOR CARRYING OUT THE INVENTION

An embodiment of the present invention will hereinafter be described. The embodiment, which will be illustrated below, is one mode of the present invention, and a technical scope of the present invention is not, however, limited to the following embodiment.

Figure 1:
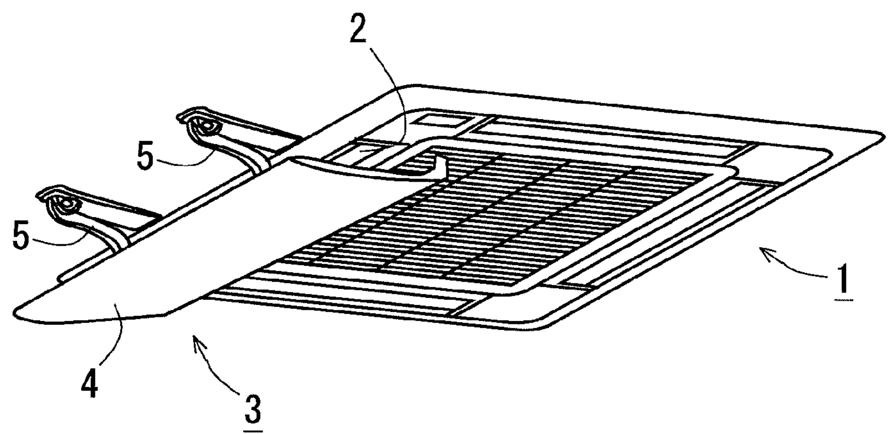
FIG. 1 illustrates a state of fitting a wind direction adjusting apparatus that adjusts a wind direction of air blown from an air conditioning blowout port of an air conditioner.

FIG. 1 illustrates a state in which to fit a wind direction adjusting apparatus 3 that adjusts a wind direction of air blown from an air conditioning blowout port 2 of an air conditioner 1. The wind direction adjusting apparatus 3 is, as illustrated in FIG. 1, disposed in front of the air conditioning blowout port 2 from which the air being air-conditioned by the air conditioner is blown, and includes: a wing plate 4 (which is one example of "a faceplate" according to the present application) that receives the air blown from the air conditioning blowout port 2; and an arm 5 (which is one example of "a fitting portion" according to the present application) for fitting the wing plate 4 to a front of the air conditioning blowout port 2.

Figure 2:
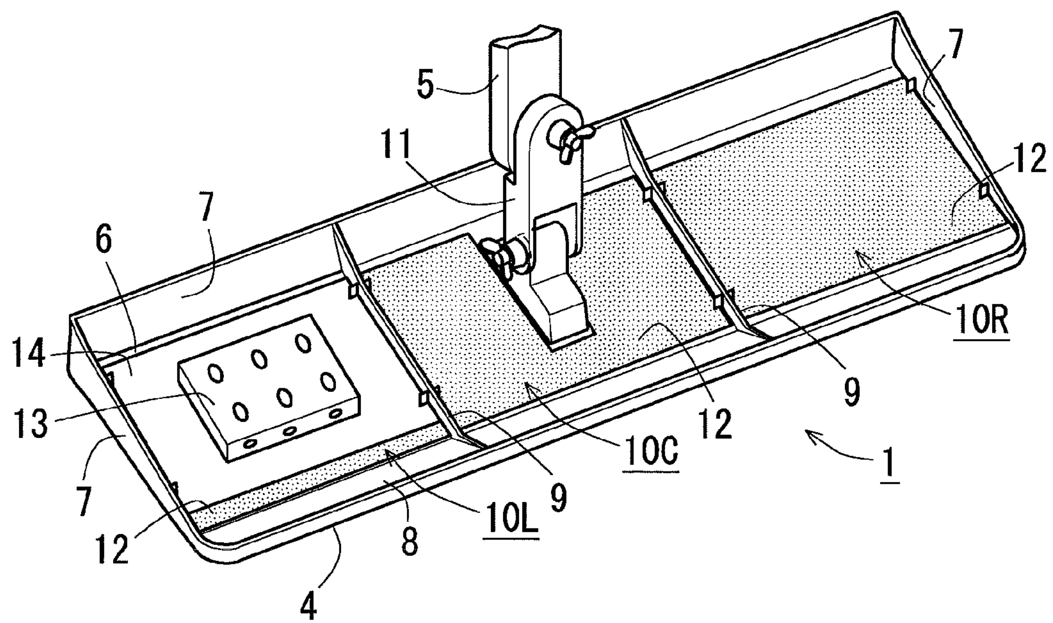
FIG. 2 is a perspective view of a wind direction adjusting apparatus.

FIG. 2 is a perspective view of the wind direction adjusting apparatus 3. The wing plate 4 is composed of plastic and other synthetic resins, and takes a shallow-bottomed container-like shape that is substantially rectangular on the whole. The wing plate 4 includes wall portions 7, 7, 7, of which both edges in a longitudinal direction and remaining one side edge excluding one side edges of a main surface portion 6 are erected at a right angle to the main surface portion 6. The wing plate 4 includes a bending portion 8, which is continuous to the main surface portion 6 and gently bent, at one side edge formed with none of the wall portions 7, 7, 7.

Reinforcing ribs 9, 9, which are erected at equal intervals along the longitudinal direction of the main surface portion 6, are provided on an upper surface of the main surface portion 6, and partition the wing plate 4 taking the shallow-bottomed container-like shape on the whole into three compartments 10L, 10C, 10R. A flexible joint 11 (which is one example of "an angle adjusting portion" according to the present application) for securing the arm 5 to the wing plate 4 biaxially rotatably, is provided in the vicinity of a central portion of the section 10C configuring the central section of the three compartments 10L, 10C, 10R. Adiabatic mats 12 for preventing dew condensation on the lower surface of the main surface portion 6 are laid in the three compartments 10L, 10C, 10R. The adiabatic mats 12 may, however, be omitted. Note that FIG. 2 omits an illustration of an upper side of the arm 5, and the arm 5, however, forks on an upper side of the flexible joint 11 and is, as illustrated in FIG. 1, secured to a portion vicinal to a border between a ceiling and the air conditioner 1.

An antibacterial member 13 is provided on the upper surface of the main surface portion 6. Note that one or more antibacterial members 13 may be provided on the upper surface of the main surface portion 6. To be specific, the antibacterial member(s) 13 may be provided in any one of the three compartments 10L, 10C, 10R, or may also be provided in the two comportments, or may further be provided in all of the partitions.

The antibacterial member 13, as depicted in FIG. 2, is pasted by an adhesive material onto a cardboard 14 superposed on the adiabatic mat 12, and is indirectly provided on the upper surface of the main surface portion 6. However, the antibacterial member 13 may be pasted directly to, e.g., the adiabatic mat 12, and may also be pasted to the main surface portion 6 of the wing plate 4 with the adiabatic mat 12 being omitted. The antibacterial member 13 may be not only pasted by the adhesive material but also attached to the wing plate 4 detachably by, e.g., a hook and loop fastener in place of the adhesive material.

Figure 3:
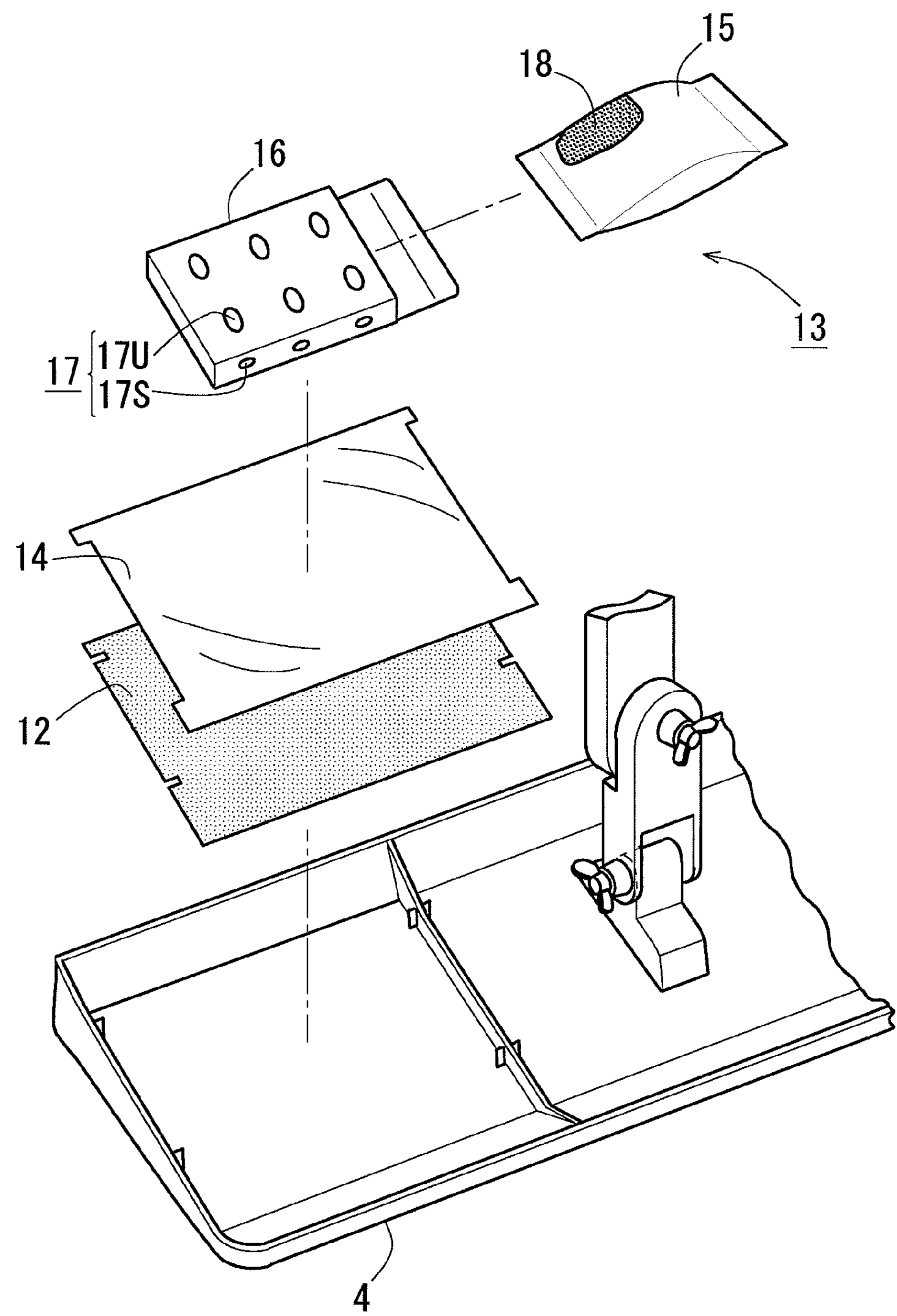
FIG. 3 illustrates one example of an exploded view of an antibacterial member.

FIG. 3 is one example of an exploded view of the antibacterial member 13. The antibacterial member 13 is, as illustrated in FIG. 3, a member including a bag body 15 and an enclosure 16. The bag body 15 contains an antibacterial agent 18 defined as a sterilizing substance that sterilizes an interior of the room. The enclosure 16 is formed with vent holes 17 to regulate a quantity of airflow of the air blown out of the air conditioning blowout port 2 and permeating the bag body 15. The enclosure 16 may be composed of paper sheets instanced by the cardboard, and may also be composed of a resin or other various types of materials. Note that FIG. 3 illustrates the rectangular parallelopiped enclosure 16, but the enclosure 16 is not limited to the rectangular parallelopiped. The enclosure 16 may be a cubic enclosure, an enclosure having a curved surface, an enclosure having triangular and pentagonal surfaces, and an enclosure taking any other shape.

The vent holes 17 are classified into upper vent holes 17U each taking an elliptical shape with its longitudinal direction extending along the airflow of the air blown out of the air conditioning blowout port 2 and being formed in the upper surface of the enclosure 16, and side vent holes 17S being formed in side surfaces of the enclosure, i.e., the side surface on an upstream side opposite to the airflow of the air blown out of the air conditioning blowout port 2 and the side surface on a downstream side positioned on an opposite side to the side surface on the upstream side. Note that FIG. 3 depicts the six upper vent holes 17U and the six side vent holes 17S, but the upper vent holes 17U and the side vent holes 17S are not limited to these numbers. A number, a size and a shape of the upper vent holes 17 are properly changeable corresponding to a flow rate of the air blown out of the air conditioning blowout port 2, a property and other equivalent characteristics of the antibacterial agent 18 contained in the bag body 15, and are determined by taking account of a tolerable amount and toxicity of the antibacterial substance to be diffused in an interior space.

Figure 4:
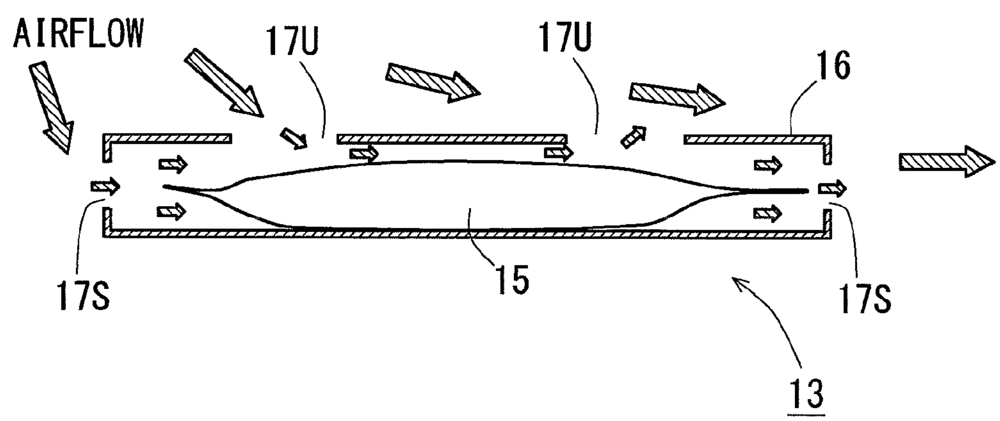
FIG. 4 illustrates one example of a view of an airflow in an interior of the antibacterial member.

FIG. 4 illustrates one example of a view of the airflow in the interior of the antibacterial member 13. In the wind direction adjusting apparatus 3, the air blown out of the air conditioning blowout port 2 flows along the upper surface of the main surface portion 6 of the wing plate 4. The air flowing into the interior of the enclosure 16 via the upper vent holes 17U and the side vent holes 17S, permeates the bag body 15. A quantity of ventilation of the air permeating the bag body 15 is regulated by the numbers, the sizes and the shapes of the upper vent holes 17U and the side vent holes 17S. Hence, the air permeating the bag body 15 flows toward the downstream of the antibacterial member 13 in a state of being added with a proper quantity of antibacterial substance. The air flowing toward the downstream side of the antibacterial member 13 is diffused in the interior space in which the wind direction adjusting apparatus 3 is installed, and sterilizes the bacteria floating in the interior space with the antibacterial substance.

Note that the enclosure 16 preferably has a size large enough to ensure a gap to such a degree to allow the air to flow along a periphery of the bag body 15 contained in the interior of at least the enclosure 16 between the bag body 15 and an internal surface of the enclosure 16. A volume ratio between the bag body 15 and the enclosure 16 is preferably, e.g., about 1:3 through 1:1.2, and more preferably about 1:2 through 1:1.2. A range being thus set enables a suitable gap to be formed between the bag body 15 and the enclosure 16, and release performance of the antibacterial substance into the air to be secured.

A particulate antibacterial agent with a porous inorganic solid carrier bearing chlorine dioxide is exemplified as a concrete example of the antibacterial agent 18 contained in the bag body 15. Such an antibacterial agent is contained therein, in which case a bag material composing the bag body 15 is preferably a material including minute holes formed over an entire surface and each having a smaller diameter than a particle size of the inorganic solid carrier. Note that the entire surface defined herein implies a degree of not exactly but substantially the whole surface of the bag body 15, and the bag body 15 partially having an area not formed with the minute holes is not, however, excluded. An antibacterial metal material and other equivalent materials, which release metallic ions in place of chlorine dioxide, may be applied as the antibacterial member 13.

Porous fine particles composed of, e.g., sepiolite are exemplified as the inorganic solid carrier bearing chlorine dioxide. A method of causing the porous fine particles composed of sepiolite to adsorb chlorine dioxide is exemplified by a method of adding an inorganic acid to an aqueous solution of sodium hydrochloride, producing chlorine dioxide by washing a generated mixture with aqueous solution of sodium hydrochloride and transforming chlorine in the mixture into chlorine dioxide, and causing this chlorine dioxide to be adsorbed to the inorganic solid carrier. Chlorine dioxide adsorbed to sepiolite dissociates from sepiolite due to physical force instanced by vibrations of the ambient air and collisions among the fine particles.

For example, when an agent with chlorine dioxide adsorbed to the porous fine particles composed of sepiolite is used as the antibacterial agent 18 contained in the bag body 15, chlorine dioxide borne by the sepiolite fine particles dissociates from surfaces of the fine particles due to the airflow of the air flowing into the enclosure 16 from the air conditioning blowout port 2, and is released outside of the bag body 15 via the minute holes formed in the entire surface of the bag body 15. Chlorine dioxide is released into the gap within the enclosure 16 having a larger volume than the bag body 15, and is control-released outside of the enclosure 16 from the vent holes 17 that regulate the ventilation quantity. Chlorine dioxide is heavier in specific gravity than the air and, upon being released into the interior space, precipitates down to the lower portion in the inside of the room. Hence, the effective sterilization in the interior space throughout is enabled by using the antibacterial agent 18 of the wind direction adjusting apparatus 3 installed at the air conditioning blowout port 2 of the air conditioner 1 installed at the ceiling. Chlorine dioxide also has efficacy of precipitating PM (Particulate Matter: which is called fine particulate matter and is instanced by PM 2.5) having an apprehension of exerting adverse influence on health down to the lower portion in the inside of the room by being adsorbed to the PM.

The wind direction adjusting apparatus 3 according to the embodiment enables the diffusion of the sterilizing substance by the airflow of the air forcibly blown out of the air conditioning blowout port 2 of the air conditioner 1, and hence eliminates a necessity for preparing a mechanical apparatus having a built-in blower and other equivalent machines for diffusing the sterilizing substance. It is feasible to diffuse the sterilizing substance in the room space throughout more surely than a simply structured product that passively diffuses the sterilizing substance, and sufficient disinfection performance can be therefore expected.

DESCRIPTION OF THE REFERENCE NUMERALS AND SYMBOLS

1 . . . air conditioner
2 . . . air conditioning blowout port
3 . . . wind direction adjusting apparatus
4 . . . wing plate
5 . . . arm
6 . . . main surface portion
7 . . . wall portion
8 . . . bending portion
9 . . . reinforcing ribs
10L, 10C, 10R . . . compartment
11 . . . flexible joint
12 . . . adiabatic mat
13 . . . antibacterial member
14 . . . cardboard
15 . . . bag body
16 . . . enclosure
17 . . . vent hole
17U . . . upper vent hole
17S . . . side vent hole
18 . . . antibacterial agent

The invention claimed is:

1. A wind direction adjusting apparatus at an air conditioning blowout port, comprising:

a faceplate being disposed in front of the air conditioning blowout port from which air being air-conditioned by an air conditioner is blown, and receiving the air blown out of the air conditioning blowout port in a flow direction;

a fitting portion fitting the faceplate to a front portion of the air conditioning blowout port;

an antibacterial member being fitted to the faceplate and including an antibacterial agent as a substance having a bactericidal property and a bag body having a bag material formed with minute holes over an entire surface, the bag body containing the antibacterial agent and the antibacterial member accommodating the bag body and having vent holes regulating a ventilation quantity of air permeating the bag body by being blown out of the air conditioning blowout port, wherein the antibacterial member is placed on an upper surface of the faceplate, and the vent holes are formed in an upper surface of an enclosure, each vent hole having an elliptical shape with a longitudinal direction of each elliptical shape extending along the upper surface of the enclosure in the flow direction of the air blown out of the air conditioning blowout port; and an adiabatic mat laid on the upper surface of the faceplate for preventing dew condensation on a lower surface of the faceplate, wherein the antibacterial member is pasted by an adhesive material onto a cardboard superposed on the adiabatic mat.

2. The wind direction adjusting apparatus of the air conditioning blowout port according to claim 1, wherein the antibacterial agent is a particulate antibacterial agent with chlorine dioxide borne on a porous inorganic solid carrier, and each of the minute holes has a diameter smaller than a particle size of the inorganic solid carrier.

3. The wind direction adjusting apparatus of the air conditioning blowout port according to claim 1, wherein the vent holes are formed in a side surface of a plurality of side surfaces of an enclosure of the antibacterial member, on an upstream side opposite to the flow of the air blown out of the air conditioning blowout port and a side surface on a downstream side positioned on an opposite side to the side surface on the upstream side.

4. The wind direction adjusting apparatus of the air conditioning blowout port according to claim 1, wherein the antibacterial member has an external shape with a thickness less than a width and a length of the antibacterial member.

5. The wind direction adjusting apparatus of the air conditioning blowout port according to claim 1, wherein an enclosure of the antibacterial member is provided with a hook and loop fastener detachably attachable to the faceplate.

6. The wind direction adjusting apparatus of the air conditioning blowout port according to claim 1, wherein the fitting portion has an angle adjusting portion enabled to adjust a fitting angle of the faceplate with respect to the air conditioning blowout port.

* * * * *